US005306231A

United States Patent [19]

Cullum et al.

[11] Patent Number: 5,306,231

[45] Date of Patent: Apr. 26, 1994

[54] TRACTION SYSTEM FOR A PATIENT IN A BED

[76] Inventors: Harry Cullum, 22 Oak St., East Hampton, N.Y. 11937; Jonathan Korn, 159 E. 69th St., New York, N.Y. 10021

[21] Appl. No.: 966,257

[22] Filed: Oct. 26, 1992

[51] Int. Cl.[5] .......... A61F 5/00

[52] U.S. Cl. .......... 602/32; 602/35

[58] Field of Search .......... 128/845, 869, 870, 874, 128/875, 846; 602/32, 33, 34, 35, 36, 38, 39, 40; 606/237, 238, 239, 240, 241, 242, 243; 269/328

[56] References Cited

U.S. PATENT DOCUMENTS

| | | | |
|---|---|---|---|
| 885,243 | 4/1908 | Haas | 602/34 |
| 2,853,999 | 9/1958 | Risser | 602/39 |
| 3,734,088 | 5/1973 | Tucker | 602/33 |
| 4,122,587 | 10/1978 | Weiss | 128/870 |
| 4,266,537 | 5/1981 | Bonin | 602/32 |
| 4,417,572 | 11/1983 | Green | 128/869 |
| 4,664,101 | 5/1987 | Granberg | 602/33 |
| 4,865,022 | 9/1989 | Gorsen | 602/33 |
| 4,911,179 | 3/1990 | Brown | 128/876 |

*Primary Examiner*—Michael A. Brown

*Attorney, Agent, or Firm*—Rosen, Dainow & Jacobs

[57] ABSTRACT

An apparatus operable in cooperation with a bed having a top surface and opposite head and foot ends for applying traction to a patient's lower back, including a lower sheet extending from the head end lengthwise to the foot end, said sheet including excess length at the head end of said bed, pulling means for pulling said lower sheet lengthwise toward the foot end of said bed, and an upper sheet having one end fixedly attached to said head end of said bed and extending lengthwise about halfway to said foot end, said upper sheet positioned above and lying on said lower sheet said pulling means adapted to periodically pull said lower sheet lengthwise in the foot end direction a predetermined distance, wherein movement of the lower sheet with the patient's buttocks and legs lying thereon effects a frictional pull in the foot end direction on said buttocks and legs, and wherein the weight of the patient's upper body on the fixed upper sheet effects a frictional resistance in the opposite direction on the patient's upper body, thus producing a tension in said lower sheet and a traction to the patient's lower back intermediate said upper body and buttocks.

14 Claims, 2 Drawing Sheets

TRACTION SYSTEM FOR A PATIENT IN A BED

This invention relates to a medical traction system for a patient in a bed and in particular to a medical apparatus traction system that can be installed on a bed.

BACKGROUND OF INVENTION

Various methods and devices are available to provide traction to a patient suffering from sciatica or low back syndrome. Typically, the patient will be positioned to be lying on his back in a bed (a male patient is assumed merely for convenience), and the patient is then secured by a harness such that the lower body, normally the pelvis or legs, is pulled in the foot end direction of the bed to apply generally axial tension to the patient's spinal system, namely the spine, vertebrae and/or muscles in that area. In a typical harness system weights are used to apply a pulling force on the pelvis, legs or ankles. Instead of or combined with such a harness there may be traction tables with sliding platform parts to exert traction on specific areas to be treated.

Regardless of how effective these systems are, each has inherent disadvantages. These apparatus are cumbersome, complicated and/or expensive. A particular problem is that the patient must be assisted into and out of the traction device by a nurse or other assistant. Thus, the typical patient cannot engage and apply the traction apparatus to himself, and such patient cannot readily disengage the apparatus himself whenever he wishes to leave the bed. With such harness and weight apparatus there is a constant danger, either from an accidental disengagement of the weights or a patient's successful self disengagement so that a weight would fall. The result could be harm to the patient or to an attending nurse, aide or doctor, or at least unplanned loss of traction.

SUMMARY OF THE INVENTION

An object of this invention is to achieve effective and safe traction of the lower back. A further object of the invention is to provide a traction apparatus so simple that it is essentially automatic and eliminates complicated and difficult-to-operate equipment, such as traction tables and harnesses. Another object of the invention is to provide a traction system which allows the patient to disengage himself from the system with no assistance and leave the bed at any time. Yet another object is the provision of a traction device of relatively low cost. These and other objects and advantages of the invention are achieved as disclosed below.

This invention uses simple friction forces resulting from the patient's own body weight applied to an axially-moving or an axially-moved bed sheet beneath the patient to produce traction in the patient's back. As the patient lies in his bed his large body parts contact and apply the greatest downward forces on the bed sheets, these large upper body parts being his upper back, head and shoulders and his buttocks, thighs and legs of the lower body. The spinal system to be placed in tension is generally intermediate these upper and lower body parts that contact the sheet. Axial friction forces are created at the areas of body contact with the lower sheet as the downward forces of the body parts are directed to the sheet and the sheet is moved axially.

Rather than attach a harness to the patient's head or upper body or to his ankles or lower body respectively, and rather than apply dead weights or spring weights or motorized forces to produce axially directed traction forces in the patient's back area, this invention, in effect, engages the patient's upper and lower body by virtue of the natural contact of these body parts with bed sheets and the frictional forces developed between the sheets and body. In the preferred embodiment separate sheets are used beneath these upper and lower body parts. The sheet under the lower body is moved axially while the other sheet remains stationary under the upper body. The downward directed weight of these body parts on the relatively moving sheets produces axial friction forces applied to the body in the direction of sheet movement. Obviously, the magnitude of the friction forces is directly related to the patient's weight. Thus, a heavier person will produce and need a greater frictional force, which can be considered in the traction force desired. The sheet beneath the lower body parts is moved axially a slight amount and held in tension thus producing a frictional "drag" on the patient's skin in contact with the sheet until the sheet stretches or slides relative to the patient's body, thus ending the tension and friction. Then the sheet is moved a slight axial distance again, each move creating a succession of temporary frictional force conditions. Alternatively, the sheet beneath the patient's lower body parts is pulled continuously very slowly, creating an essentially constant axial frictional force.

In accordance with the invention a device is configured with means for attachment to a bed. A lower sheet extending lengthwise beyond the ends of the bed is provided. Excess sheet is stacked at the head end. The opposite end of the lower sheet is wound around a take-up roller, which is rotatably supported at the foot end of the bed. An upper sheet having one end fixedly attached to the head of the bed for accommodating the patient's head and back, extends in the foot direction about one half the length of the bed and is positioned above and lying on the lower sheet. Sheet movement means are operatively connected with the rotatable support means for pulling a length of lower sheet from the excess sheet stack onto the bed and for moving the lower sheet longitudinally along the bed a predetermined distance in the direction of the take-up roller or for moving the lower sheet lengthwise at a predetermined rate. The weight of the patient's back and head on the fixed upper sheet exerts a frictional resistance on the patient's upper body thus providing friction to resist the opposite friction force produced by the lower sheet on the buttocks and legs.

BRIEF DESCRIPTION OF THE DRAWINGS

The invention will now be described in greater detail with reference to the accompanying drawings, wherein.

DETAILED DESCRIPTION OF THE PREFERRED EMBODIMENTS

Figure 1:
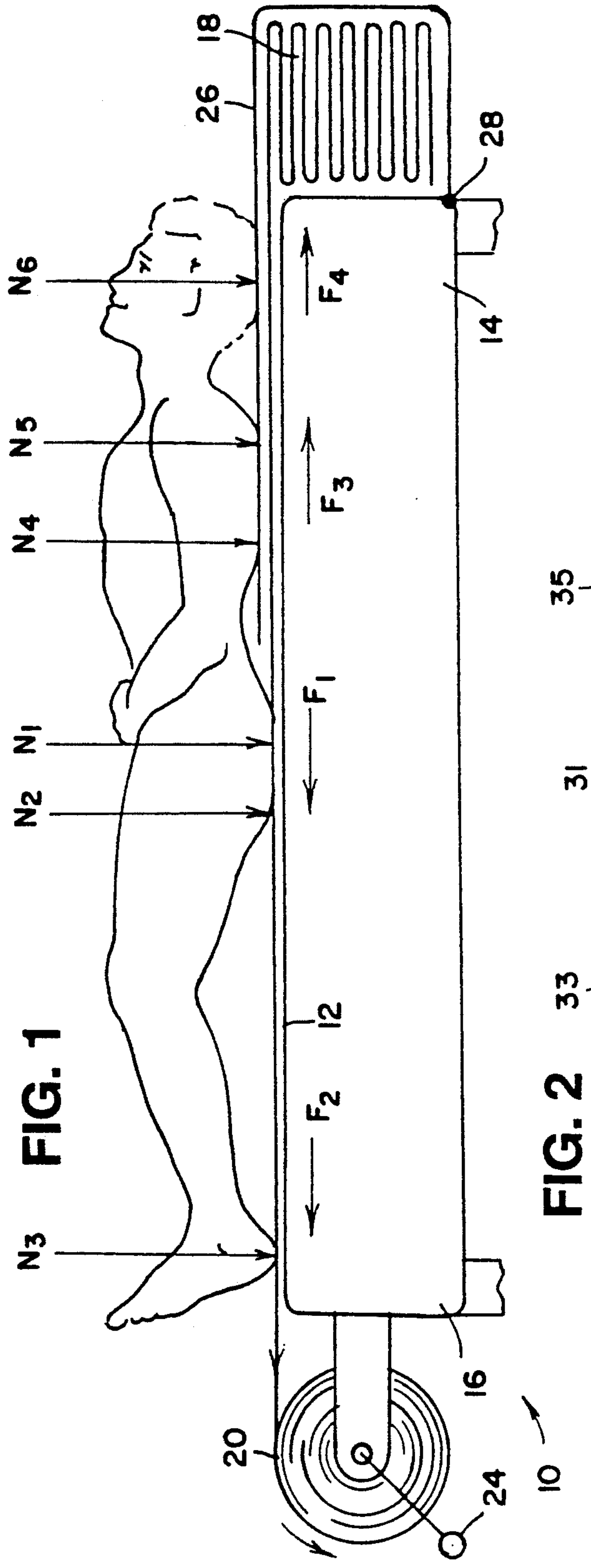
FIG. 1 is a side elevation view of the traction system of the invention.

FIG. 1 shows a bed 10 representing a hospital bed or a standard bed. While the widest use of the invention is expected to be on hospital beds, it will work equally well on conventional beds.

In accordance with the invention there is provided a lower sheet 12 comprising a continuous strip extending from the head end 14 of the bed lengthwise to the foot end 16. This sheet has excess length which is stacked adjacent to and exterior to the head of the bed in a fan-fold configuration 18 or it may be furled or rolled. At the foot end the sheet 12 is attached to a take-up roller 20 or to other pulling means. The preferred length of the sheet is approximately fourteen feet, but it may vary depending on the expected duration of traction. The width of the sheet is approximately the same as or slightly greater than the width of the bed. Preferably there is a high friction upper surface on this sheet, such as a rubber sheet or a fabric sheet with a rubberized surface.

The fan-fold supply of sheet 18 may be replaced by a roller (not shown) on which sheet is rolled with suitable brackets at the sides of the bed and exterior thereto for supporting the roller and for easily receiving the roller. With less mechanism involved the cost is obviously reduced. In a simpler embodiment there is neither fan-fold nor head end roller supply because only about thirty six inches of lower sheet length (from the head end to the patient's hips) is used to establish the traction force.

The take-up roller 20 is made of metal or plastic and is located adjacent the foot of the bed and exterior thereto. The roller is rotatably supported by a pair of brackets 22 spaced laterally of the bed. The roller will be driven by power means such as an electric motor (not shown) connected directly to the roller or by other transmission means. A ratchet and pawl arrangement (not shown) may serve as a releasable lock.

A second sheet 26 extends from the head end lengthwise about one half the length of the bed above the lower sheet. This second sheet has one end fixedly secured at 28 to the head of the bed. This upper sheet is positioned parallel to and in contacting relation with the lower sheet. FIG. 1 shows a small vertical space between the upper and lower sheets and a similar small vertical space between the lower sheet and the top of the bed. This is for clarity of this disclosure; in reality no such spaces would be visible.

In operation of this invention the patient lies on the bed with his upper body, namely his head and back supported on the fixed upper sheet, and with his lower body, namely his buttocks and legs supported on the movable lower sheet.

In operation the motor is energized to rotate the roller and cause the lower sheet to be moved a predetermined distance or at a predetermined rate. With the predetermined distance version of this apparatus the lower sheet is pulled or drawn from the excess sheet stack longitudinally a predetermined distance in the direction of the take-up roller. The patient should be lying on his or her back with knees slightly raised so that the leg and thigh below and above the knee respectively define an angle of about 120°. The weight of the patient's lower body produces downward (normal) forces $N_1$, $N_2$ and $N_3$ from the buttocks, thighs and legs or feet respectively. The movement of the lower sheet at the areas of contact with forces $N_1$, $N_2$ and $N_3$ produces friction forces $F_1$, $F_2$ and $F_3$ respectively on the patient's lower body. At the same time the weight of the patient's upper back, shoulders and head on the fixed upper sheet exerts normal forces $N_4$, $N_5$ and $N_6$ downward which produce friction forces $F_4$, $F_5$ and $F_6$ on the patient's upper body in the opposite direction as $F_1$, $F_2$ and $F_3$. These oppositely directed friction forces produce traction on the patient's back in areas intermediate $N_1$ and $N_2$.

Typically with this predetermined distance version the lower sheet will move approximately one inch every fifteen to thirty minutes after initial traction is applied. As the roller is turned it puts tension on the lower sheet until this sheet begins to slide slightly along the bed, i.e. until the lower sheet overcomes static frictional resistance. Just as the sheet starts to slide, pulling of the sheet is stopped and the roller is locked in position by the ratchet and pawl or by other means to prevent reverse motion. While the lower sheet is tightly drawn it engages and pulls the patient's skin at all points of contact producing the tractional force. After about 10 to 15 minutes the traction device must be reset and traction readjusted to correct for displacement of the sheet due to patient movement, sheet stretching or sliding, or any other disruption in the tight contact between the lower sheet and the patient. The tension of the sheet is readjusted so that it again is stretched tightly against the patient's skin or patient's clothing if he is wearing same. To achieve this readjustment the patient may push a button for controlling a motor, or drive a manual crank or lever, or have still other assistance.

The sheet may be readjusted by driving the roller for as long as necessary to tighten the sheet to the point where the sheet begins to slide in the direction of the take-up roller. This is usually about 1-2 inches.

Alternatively, the take-up roll may be power actuated by the motor described above in combination with a tensiometer or other sensing means which measures the tension of the sheet. Means responsive to the tensiometer are provided for activating the sheet movement drive means when the tension of said sheet declines to a predetermined level. In response to an appropriate signal from the tensiometer the drive means again pulls the sheet a predetermined distance in the direction of said take-up roller. It is further contemplated that automatic timing means may be provided for activating the drive means to periodically reset the traction apparatus. For example, the lower sheet could be pulled an additional one inch about every fifteen minutes.

Instead of moving the lower sheet a predetermined distance, the apparatus may move the lower sheet at a very slow but constant rate of lengthwise travel. Here the rate would be in the range of one half to four inches per hour.

Typically, conventional traction involving a harness arrangement produces about ten to fifteen pounds of applied force. Since much of the force is resisted by muscle and friction of the buttocks on the bed, an effective force of five pounds or less of traction is actually exerted. This friction of the buttocks on the bed is beneficially utilized by the present device. The device of the present invention applies an effective, prolonged force of approximately five pounds force of traction, useful in treating sciatica or low back syndrome. The force additionally tends to decrease lumber lordosis by producing a force moment that rotates the pelvis which is an objective in this treatment of sciatica. Prior traction devices do not do this, namely they pull and may even rotate the pelvis in the wrong direction. Beneficial rotation tends to flatten the small of the back, which is a standard exercise in physical therapy.

Optimally, it is contemplated that the patient be nude when using this traction device; however, the patient may wear pajamas or other items of clothing provided that appropriate belts are used which secure the clothing from being pulled off or moved excessively lengthwise due to the sheet motion.

When the lower sheet is axially moved until it passes beyond the patient's buttocks, or when treatment on a particular patient is completed this sheet is removed for cleaning by removing the take-up roller. For brief treatment it is possible to use a short length of lower sheet that is situated primarily only beneath the patient's buttocks and does not extend toward the head-end of the bed. A further variation would be to reduce friction between the bottom of the upper sheet and the top of the lower sheet where they overlap beneath the patient's upper body.

Figure 2:
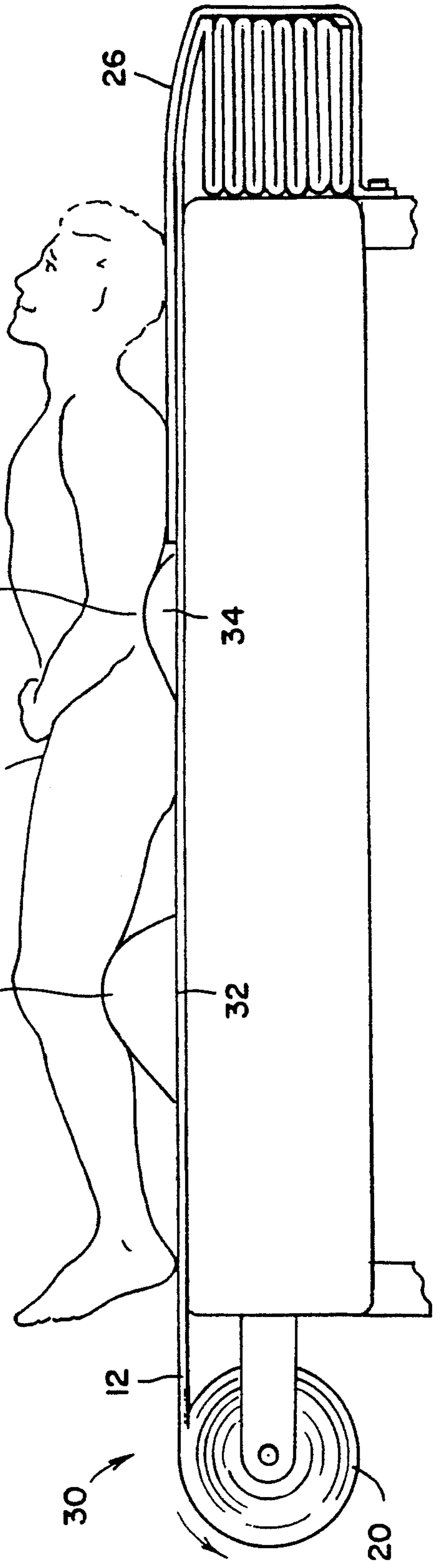
FIG. 2 is a side elevation of a second embodiment showing wedge-shaped pads in a small of back and under bent knees.
Figure 3:
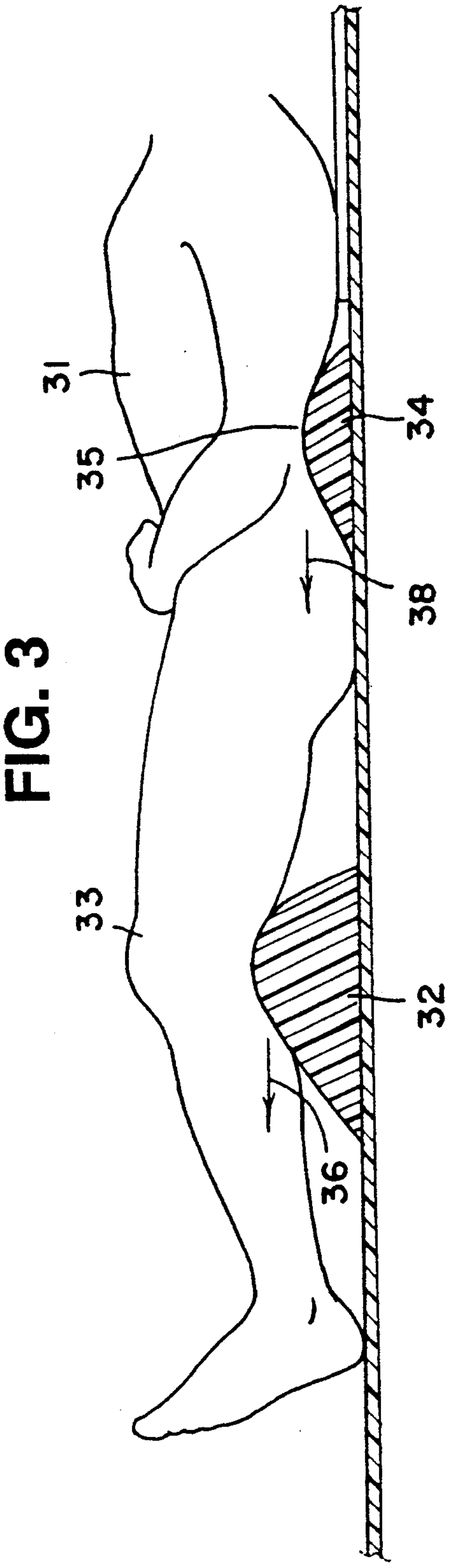
FIG. 3 is an enlarged fragmentary view of the patient and pads of FIG. 2.

FIGS. 2 and 3 show schematically a second embodiment 30 that is generally similar to the system of FIG. 1 and uses the same reference numbers for the same elements but adds one or two wedge shaped pads 32, 34 positioned under the knees 33 and back 35 respectively of a patient 31 if greater traction is required. Either or both pads may be used. Each of the pads used is secured to the lower sheet 12. Pad 32, for example, when positioned beneath the patient's knees is situated to push in the direction of arrow 36, generally axially against the rear surface of the calf.

Thus, the frictional forces due to the sheet are supplemented by a pushing of the pad against the natural barrier formed by the calf. Thus, traction on the back is increased without the need of a harness, weights or other conventional techniques.

Pad 34 beneath the back when moved by the sheet similarly pushes axially against the rear surface of the upper portion of the buttocks or hip area generally in the direction of arrow 38. Like pad 32 the pad 34 supplements the sheet's frictional force in the axial direction by a direct pushing force, again without need of a harness, weights or other apparatus that must be attached to the patient.

The pads 32 and/or 34 may be wedge-shaped cushions covered with cotton or other fabric and filled with foam rubber, feathers, or other material. These pads may be secured to sheet 12 by a variety of permanent or removable techniques, including sewing or gluing or use of Velcro® brand fastening means between adjacent surfaces of a pad and the sheet. It is further possible to use the sheet with one or more pads as a principal means of developing the traction forces instead of the friction forces from contact with the sheet 12. A wedge as shown can apply a pushing force as described and also a friction force generally as described for the sheet without a wedge. The pads would have to be repositioned periodically.

Figure 4:
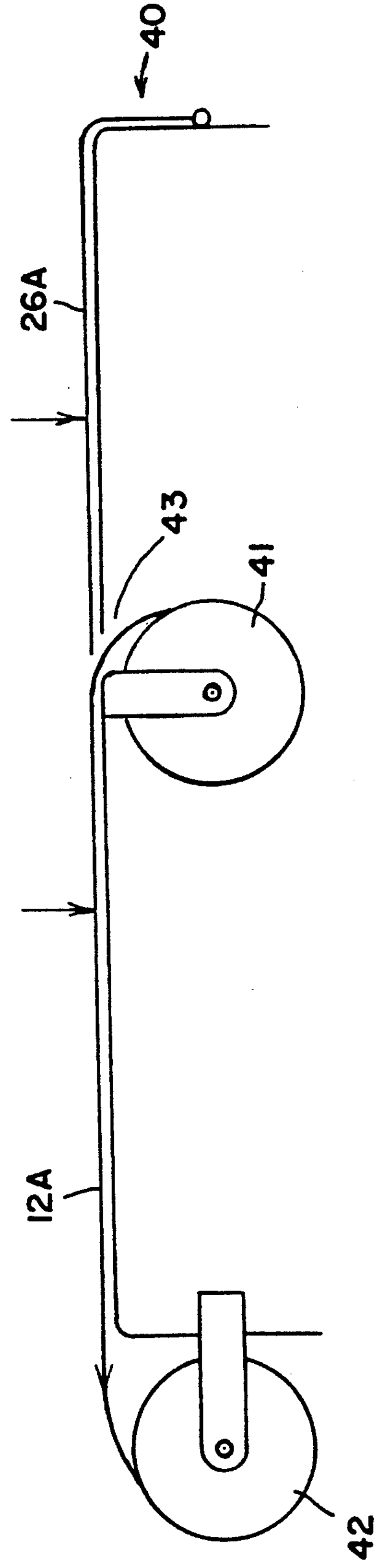
FIG. 4 is a side elevation view of a third embodiment of this invention.

FIG. 4 shows schematically a further variation 40 of the system of FIG. 1 not intended for a standard bed in the home. Here the lower sheet 12A is supplied from supply roller 41 to take-up roller 42. As shown, there must be provision such as an opening 43 in the surface of the bed for sheet 12A to emerge from roller 41 and then be extended to take up roller 42. With this arrangement the lower sheet 12A does not travel beneath the upper sheet 26A, as seen in FIGS. 1 and 2. An obvious disadvantage of the FIG. 4 embodiment is that due to the required opening 43, it cannot be used as an attachment to a conventional bed. While not shown, this apparatus would be driven similarly as the FIG. 1 system with a motor or crank.

While the invention has been described in connection with the preferred embodiments, this is not meant to be limiting, and other variations will be evident to those skilled in the art and are deemed to be within the scope of the invention. For instance, the position of the patient may be reversed so that the moving sheet is applied to the upper rather than the lower body.

We claim:

1. For cooperation with a bed having a top surface and opposite head and foot ends, an apparatus for applying traction to a patient's lower back, comprising:
   a—a lower sheet extending from the head end lengthwise to the foot end, said sheet including excess length at the head end of said bed,
   b—pulling means for pulling said lower sheet lengthwise toward the foot end of said bed, and
   c—an upper sheet having one end fixedly attached to said head end of said bed and extending lengthwise about halfway toward said foot end, said upper sheet positioned above and lying on said lower sheet, said pulling means adapted to periodically pull said lower sheet lengthwise in the foot end direction a predetermined distance, wherein movement of the lower sheet with the patient's buttocks and legs lying thereon effects a frictional pull in the foot end direction on said buttocks and legs, and wherein the weight of the patient's upper body on the fixed upper sheet effects a frictional resistance in the opposite direction on the patient's upper body, thus producing a tension in said lower sheet and a traction to the patient's lower back intermediate said upper body and buttocks.

2. The apparatus according to claim 1 wherein said predetermined distance is about one to two inches.

3. The apparatus of claim 1 wherein said pulling means comprises a take-up roller on which a portion of said sheet is rolled and manual or motorized drive means for rotating said take-up roller.

4. The apparatus of claim 3 further comprising locking means operative in connection with said pulling means to prevent reverse movement of said take-up roller.

5. The apparatus of claim 1 wherein said excess length of sheet is positioned in a fan-fold configuration near said head end of the bed.

6. The apparatus of claim 4 wherein said predetermined distance comprises the distance required to pull the lower sheet taut until such movement when said sheet overcomes static friction with the patient and begins to slide in the direction of said take-up roller.

7. The apparatus of claim 1, further comprising means for sensing the tension of said lower sheet, and means responsive to said sensing means for activating said pulling means when the tension of said sheet declines to a predetermined level, said pulling means then pulling said sheet a predetermined distance in the foot end direction.

8. The apparatus of claim 1 further comprising timing means and means responsive to said timing means for activating said pulling means to periodically reset the pulling means.

9. The apparatus of claim 1 wherein said pulling means produces an effective, prolonged tractional force of about five pounds applied to the patient's lower back.

10. Apparatus according to claim 1 further comprising a first wedge means secured to the upper surface of said lower sheet and projecting upward therefrom, whereby said first wedge means becomes positioned beneath the patient's lower back, and when the sheet and said first wedge means are pulled in the foot end direction said first wedge means presses in said direction against the patient's buttocks applying a force in said foot end direction.

11. Apparatus according to claim 10 further comprising a second wedge means secured to the upper surface of said lower sheet and projecting upward therefrom, whereby the second wedge means becomes positioned beneath the patient's knees, and when the sheet and second wedge means are pulled in the foot end direction the second wedge means presses in aid foot end direction against the back of the legs applying a force in said foot end direction.

12. Apparatus according to claim 1 further comprising a second wedge means secured to the upper surface of said lower sheet and projecting upward therefrom, whereby the second wedge means becomes positioned beneath the patient's knees, and when the sheet and second wedge means are pulled in the foot end direction the second wedge means presses in said direction against the back of the legs applying a force in said foot end direction.

13. In cooperation with a bed having a top surface and opposite head and foot ends, an apparatus for applying traction to a patient's lower back, comprising:

a—a lower sheet extending from the head end lengthwise to the foot end, said sheet including excess length at the head end of said bed, b—pulling means for pulling said lower sheet lengthwise toward the foot end of said bed, and c—an upper sheet having one end fixedly attached to said head end of said bed and extending lengthwise about halfway to said foot end, said upper sheet positioned above and lying on said lower sheet, d—pulling means adapted to pull said lower sheet lengthwise in the foot end direction a predetermined rate, wherein movement of the lower sheet with the patient's buttocks and legs lying thereon effects a frictional pull in the foot end direction on said buttocks and legs, and wherein the weight of the patient's upper body on the fixed upper sheet effects a frictional resistance in the opposite direction on the patient's upper body, thus producing traction to the patient's sciatic or lower back area intermediate said upper back and buttocks.

14. A method of applying a longitudinally directed friction force to a patient's lower back area, this method operable with a bed having a top surface and head and foot ends, the method comprising the steps:

a—providing a first sheet that is longer than the length of the bed with the excess length of the sheet at or near the head end, b—providing a second sheet that extends from the head end about half way to the foot end and lies above said first sheet, c—positioning the patient to lie on his back on the bed with his upper back and head contacting said second sheet and his buttocks and legs contacting said first sheet, whereby his upper back and buttocks apply downward forces on the respective sheets, and d—pulling said first sheet lengthwise toward the foot end of the bed, thereby applying a lengthwise frictional force in the foot end direction to said buttocks and legs, while the weight of the patient's upper back and head on the second sheet causes a separate friction force in the opposite head end direction to said upper back and head, said oppositely directed friction forces producing a traction force on the patient's lower back area intermediate said upper back and buttocks.

* * * * *